United States Patent [19]

Chang et al.

[11] Patent Number: 4,696,959
[45] Date of Patent: Sep. 29, 1987

[54] MODIFIED PIPERIDINES AS ULTRAVIOLET LIGHT STABILIZERS

[75] Inventors: Wen-Hsuan Chang; Michael M. Chau; Robert Piccirilli, all of Gibsonia, Pa.

[73] Assignee: PPG Industries, Inc., Pittsburgh, Pa.

[21] Appl. No.: 536,143

[22] Filed: Sep. 26, 1983

[51] Int. Cl.$^4$ .................. C08K 5/34; C09K 15/16; C08F 82/80; C07D 251/00

[52] U.S. Cl. ................................ 524/91; 252/401; 524/99; 524/100; 524/102; 524/103; 525/162; 525/328.8; 525/375; 525/157; 528/253; 528/254; 528/258; 546/187; 546/188; 546/189; 546/190; 546/210; 544/198

[58] Field of Search ............ 524/99, 100, 102, 103, 524/91, 100; 525/162, 328.8, 375, 157, 509, 181, 375; 528/253, 254, 258, 138, 163; 546/190, 199, 187, 188, 189, 187, 210; 252/401; 544/198

[56] References Cited

U.S. PATENT DOCUMENTS

| | | |
|---|---|---|
| 2,822,347 | 2/1958 | Wohnsiedler ............... 260/67.6 |
| 3,640,928 | 2/1972 | Murayama et al. ............ 260/23 X |
| 4,014,887 | 3/1977 | Randell et al. ............ 260/293.84 |
| 4,021,432 | 5/1977 | Holt et al. ............ 260/293.64 |
| 4,049,647 | 9/1977 | Holt et al. ............ 546/187 |
| 4,086,204 | 4/1978 | Cassandrini et al. ....... 260/45.8 NT |
| 4,102,870 | 7/1978 | Hofmann et al. ............ 528/73 |
| 4,108,829 | 8/1978 | Cassandrini et al. ....... 260/45.8 NT |
| 4,141,883 | 2/1979 | Soma et al. ............ 260/45.8 N |
| 4,161,592 | 7/1979 | Evans et al. ............ 544/198 |
| 4,177,186 | 12/1979 | Rody et al. ............ 260/45.8 N |
| 4,210,578 | 7/1980 | Rody et al. ............ 260/45.8 N |
| 4,223,147 | 9/1980 | Oertel et al. ............ 524/100 |
| 4,234,728 | 11/1980 | Rody et al. ............ 524/100 |
| 4,254,235 | 3/1981 | Turpin ............ 525/162 |
| 4,262,033 | 4/1981 | Massy et al. ............ 525/162 |
| 4,273,695 | 6/1981 | Greene et al. ............ 525/162 |
| 4,288,593 | 9/1981 | Rody ............ 544/198 |
| 4,299,926 | 11/1981 | Rody et al. ............ 525/55 |
| 4,310,450 | 1/1982 | Wang et al. ............ 524/91 |
| 4,321,374 | 3/1982 | Morimura et al. ............ 544/198 |
| 4,344,876 | 8/1982 | Berner ............ 524/91 |
| 4,348,493 | 9/1982 | Loffelman ............ 524/100 |
| 4,356,287 | 10/1982 | Loffelman et al. ............ 525/204 |
| 4,370,430 | 1/1983 | Hoffman ............ 524/96 |
| 4,386,177 | 5/1983 | Loffelman ............ 524/100 |
| 4,387,194 | 6/1983 | Ottaviani et al. ............ 525/454 |
| 4,418,000 | 11/1983 | Zannucci et al. ............ 252/403 |
| 4,418,001 | 11/1983 | Zannucci et al. ............ 252/403 |
| 4,426,471 | 1/1984 | Berner ............ 524/91 |

FOREIGN PATENT DOCUMENTS 0047967  3/1982  European Pat. Off. .

Primary Examiner—John Kight
Assistant Examiner—Kriellion Morgan
Attorney, Agent, or Firm—Linda Pingitore

[57] ABSTRACT

A composition of matter contains as a principal component a material which acts as an ultraviolet light stabilizer. The ultraviolet light stabilizer is formed from the reaction of (a) a methylol or alkoxy alkyl-containing material, and (b) an alkyl substituted piperidine containing material which is represented by the following structural formula:

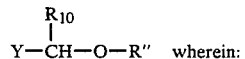

Y—CH—O—R''  wherein:

R'' is hydrogen or $C_1$ to $C_6$ alkyl,
$R_{10}$ is hydrogen or methyl,
Y is a radical derived from a material selected from the group consisting of amino substituted triazines, ureas, glycolurils, phenols, and amides of the formula

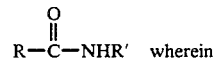

R—C—NHR'  wherein R' is hydrogen or $C_1$ to $C_{12}$ alkyl and R is an aliphatic, cycloaliphatic, or olefinic radical, or an acrylic polymer moiety having at least one group selected from hydroxyl, carboxyl, amido, and ureido, said reaction proceeding between a methylol or alkoxy alkyl group of (a) and the group selected from hydroxyl, carboxyl, amido and ureido of (b).

16 Claims, No Drawings

MODIFIED PIPERIDINES AS ULTRAVIOLET LIGHT STABILIZERS

BACKGROUND OF THE INVENTION

A large variety of polymeric materials which are utilized as the resinous component both in coating compositions and molding compositions for molded plastics are light sensitive, hence they must be protected from ultraviolet light in order to prevent degradation of the polymer in the final product. Typically, materials known as ultraviolet light stabilizers are incorporated into the coating or molding composition to inhibit the effects of ultraviolet light. A particularly well known and effective group of such materials are sterically hindered piperidine compounds, for example, materials containing the moiety 2,2,6,6-tetramethyl piperidine. However, sterically hindered piperidines of this type readily elute from the composition containing them, and in addition, they pose problems in handling and use. Moreover, coatings containing them have a tendency to exhibit blooming.

To overcome these difficulties, efforts have been directed toward chemically incorporating the ultraviolet light stabilizer into the polymeric backbone of the material to be protected. For example, U.S. Pat. No. 4,102,870 to Hoffman is directed to a manner of chemically incorporating hindered piperidine derivatives into a thermoplastic polyurethane polymer and U.S. Pat. No. 4,234,728 to Rody et al deals with the chemical incorporation of hindered piperidines into thermosetting compositions. The manner of incorporating the substituted piperidine moiety into thermosetting compositions is not easily accomplished and in addition can be relatively expensive. There is a need, therefore, for a simple, economical manner of incorporating ultraviolet light stabilizers into thermosetting compositions, particularly aminoplast curable compositions.

SUMMARY OF THE INVENTION

In accordance with the present invention there is provided a composition of matter which comprises a material formed from the reaction of:
(a) a methylol or alkoxy alkyl-containing material; and
(b) an alkyl substituted piperidine-containing material which is represented by the following structural formula:

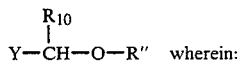
Y—CH—O—R″ wherein:

R″ is hydrogen or $C_1$ to $C_6$ alkyl,
$R_{10}$ is hydrogen or methyl,
Y is a radical derived form a material selected from the group consisting of amino substituted triazines, ureas, glycolurils, phenols, and amides of the formula

R—C—NHR′ wherein

R′ is hydrogen or $C_1$ to $C_{12}$ alkyl and R is an aliphatic, cycloaliphatic, or olefinic radical, or an acrylic polymer moiety having at least one group selected from hydroxyl carboxyl, amido, and ureido, said reaction proceeding between a methylol or alkoxy alkyl group of (a) and the group selected from hydroxyl, carboxyl, amido and ureido of (b).

Also provided in accordance with the present invention is a composition of matter which comprises a material having the following structural formula:

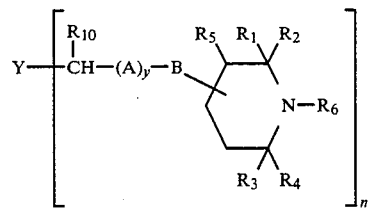

wherein:
Y is a radical derived from a material which is capable of reacting with formaldehyde to form methylol groups;
$R_1$, $R_2$, $R_3$, $R_4$ are the same or different $C_1$ to $C_6$ alkyl; and $R_1$ and $R_2$ when joined together form a $C_3$ to $C_{12}$ cycloaliphatic ring;
$R_5$ is hydrogen or methyl;
$R_6$ is hydrogen, O·, $C_1$ to $C_{12}$ alkyl, hydroxyl, $C_2$ to $C_{18}$ alkenyl or alkynyl, $C_7$ to $C_{18}$ aralkyl, acyl, carbamoyl, benzyl, or a group $$+(CH_2)_q HC—O—]_w H$$
$$\quad\quad\quad | $$
$$\quad\quad\quad R_7$$

wherein $R_7$ is hydrogen, methyl, ethyl, phenyl, or $CH_2OR_8$, q is an integer from 1 to 3 and w is an integer from 1 to 10 and $R_8$ is $C_1$ to $C_6$ alkyl or phenyl;
$R_{10}$ is methyl or hydrogen;
B is oxygen or

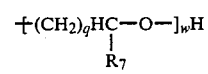

wherein $R_{11}$ is hydrogen, $C_1$ to $C_4$ alkyl, —(A)$_y$—H, or

A is

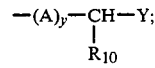

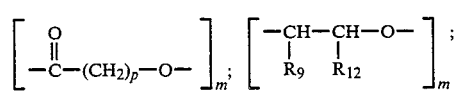

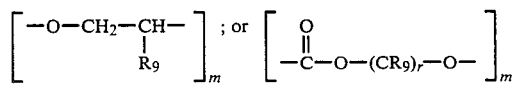

wherein $R_9$ and $R_{12}$ are independently hydrogen or $C_1$ to $C_{10}$ alkyl; m is an integer from 1 to 10; p is an integer from 1 to 5; r is an integer from 2 to 3; n is an integer from 1 to 6; and y is 0 or 1, with the proviso that when B is y is 1.

Also provided in accordance with the present invention is a process for the preparation of a hindered amine stabilizer, comprising:

contacting a methylol or alkoxy alkyl-containing material with an alkyl substituted piperidine-containing material of the structure:

$$H-(A)_y-B\underset{R_3\ R_4}{\overset{R_5\ R_1\ R_2}{\diagdown\!\!\diagup}}N-R_6$$

under conditions sufficient to transetherify and eliminate water or alcohol, thereby forming a hindered amine stabilizer having the following structural formula:

$$Y-\left[\underset{R_{10}}{\overset{|}{CH}}-(A)_y-B\underset{R_3\ R_4}{\overset{R_5\ R_1\ R_2}{\diagdown\!\!\diagup}}N-\right]_n$$

wherein:

Y is a radical derived from a material which is capable of reacting with formaldehyde to form methylol groups;

$R_1$, $R_2$, $R_3$, $R_4$ are the same or different $C_1$ to $C_6$ alkyl; and $R_1$ and $R_2$ when joined together form a $C_3$ to $C_{12}$ cycloaliphatic ring;

$R_5$ is hydrogen or methyl;

$R_6$ is hydrogen, O., $C_1$ to $C_{12}$ alkyl, hydroxyl, $C_2$ to $C_{18}$ alkenyl or alkynyl, $C_7$ to $C_{18}$ aralkyl, acyl, carbamoyl, benzyl, or a group $$+(CH_2)_q\underset{R_7}{\overset{|}{HC}}-O-]_wH$$

wherein $R_7$ is hydrogen, methyl, ethyl, phenyl, or $CH_2OR_8$, q is an integer from 1 to 3 and w is an integer from 1 to 10 and $R_8$ is $C_1$ to $C_6$ alkyl or phenyl;

$R_{10}$ is hydrogen or methyl;

B is oxygen or $$\underset{|}{-\overset{R_{11}}{N}-},$$

wherein $R_{11}$ is hydrogen, $C_1$ to $C_4$ alkyl, $-(A-)_y-H$, or $$-(A)_y-\underset{R_{10}}{\overset{|}{CH}}-Y;$$

A is $$\left[-\overset{O}{\overset{\|}{C}}-(CH_2)_p-O-\right]_m;\ \left[\underset{R_9\ R_{12}}{\overset{-CH-CH-O-}{|\ \ \ \ |}}\right]_m;$$

$$\left[\underset{R_9}{\overset{-O-CH_2-CH-}{|}}\right]_m;\ or\ \left[-\overset{O}{\overset{\|}{C}}-O-(CR_9)_r-O-\right]_m$$

wherein $R_9$ and $R_{12}$ are independently hydrogen or $C_1$ to $C_{10}$ alkyl; m is an integer from 1 to 10; p is an integer from 1 to 5, r is an integer from 2 to 3; n is an integer from 1 to 6; and y is 0 or 1, with the proviso that when B is $$\underset{|}{-\overset{R_{11}}{N}-},$$

y is 1.

There is also provided an improved resinous thermosetting composition comprising an active hydrogen-containing material and a curing agent reactive with the active hydrogens to form a cured product, the improvement comprising including in the composition a hindered amine of the formula set forth above.

DETAILED DESCRIPTION OF THE INVENTION

The composition of matter of the present invention comprises an alkyl substituted piperidine derivative (also termed a hindered amine) which functions as an ultraviolet light stabilizer. The ultraviolet light stabilizing material is formed from the reaction of:

(a) a methylol or alkoxy alkyl-containing material; and (b) an alkyl substituted piperidine-containing material having at least one group selected from hydroxyl carboxyl, amido, and ureido.

The methylol or alkoxy alkyl-, preferably alkoxy methyl-, containing material can be represented by the structural formula:

$$Y-\underset{R_{10}}{\overset{|}{CH}}-O-R$$

wherein Y is a radical derived from a material capable of reacting with formaldehyde to form at least one methylol group; and R can be hydrogen, $C_1$ to $C_6$ alkyl or $C_6$ to $C_{18}$ aryl; and $R_{10}$ can be hydrogen or methyl. As was mentioned above, preferably R is methyl. In addition, preferably $R_{10}$ is hydrogen.

The alkyl substituted piperidine-containing material having at least one group selected from hydroxyl, carboxyl, amido and ureido can be represented by the following structural formula:

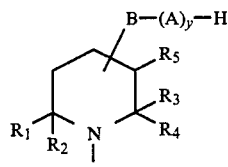 (I)

In the above formula, B is oxygen or

wherein $R_{11}$ is hydrogen, $C_1$ to $C_4$ alkyl, $-(A)_y-H$, or

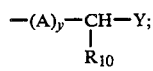

$R_1$, $R_2$, $R_3$, $R_4$ are the same or different $C_1$ to $C_6$ alkyl groups such as methyl, ethyl, propyl, butyl, pentyl and hexyl. Also, $R_1$ and $R_2$ when joined together can form a $C_3$ to $C_{12}$ cycloaliphatic ring. $R_5$ can be hydrogen or methyl. Preferably, $R_1$, $R_2$, $R_3$, $R_4$ are methyl and $R_5$ is hydrogen. A in the aforesaid formula can be represented by the following groups:

A is

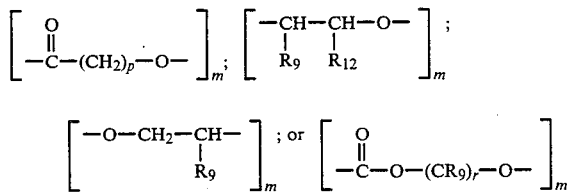

wherein: $R_9$ and $R_{12}$ are independently hydrogen or $C_1$ to $C_{10}$ alkyl, m is an integer from 1 to 10, p is an integer from 1 to 5, r is an integer from 2 to 3; and y is 0 or 1, with the proviso that when B is

y is 1.

Generally, in the above formula N, which forms the piperidine ring, is further substituted with $R_6$, wherein $R_6$ can be hydrogen, O., $C_1$ to $C_{12}$ alkyl, hydroxyl, $C_2$ to $C_{18}$ alkenyl or alkynyl, $C_7$ to $C_{18}$ aralkyl, acyl, carbamoyl, benzyl, or a group

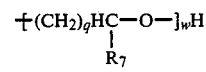

wherein: $R_7$ is hydrogen, methyl, ethyl, phenyl or $CH_2OR_8$, q is an integer from 1 to 3, w is an integer from 1 to 10, and $R_8$ is $C_1$ to $C_6$ alkyl or phenyl. Exemplary of the aforesaid substituents include methyl, ethyl, n-propyl, 2-ethylhexyl, n-nonyl, allyl, 2-butenyl, 2-pentenyl, acetyl, benzoyl, methyl carbamoyl, and hydroxyethyl. Preferably $R_6$ is hydrogen or methyl.

The materials from which Y, above, is derived are those which are capable of reacting with formaldehyde to form methylol groups. Examples of such materials include amino substituted triazines such as melamine, or benzoguanamine; ureas; glycolurils; phenols; and amides of the formula

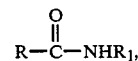

wherein R can be an aliphatic, cycloaliphatic, aromatic or olefinic radical, or an acrylic polymeric moiety such as a copolymer of methyl methacrylate and acrylamide. $R_1$ can be hydrogen or a lower aliphatic radical such as $C_1$ to $C_{12}$ alkyl, for example acrylamide. Also useful are copolymers of acrylamide with ethylenically unsaturated monomers.

The materials capable of reacting with formaldehyde to form methylol groups which have been exemplified above are described in detail below.

Melamine, or more specifically, 1,3,5 triamino triazine is a cyclic trimer of cyanamide. It possesses six replaceable hydrogens and thus is hexafunctional in its reactions with formaldehyde to form melamineformaldehyde condensates. The following reaction sequence is illustrative.

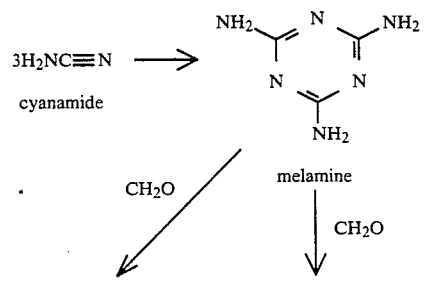

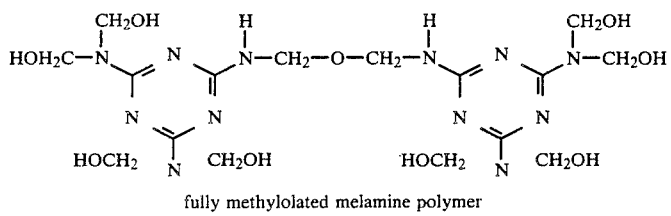

fully methylolated melamine polymer

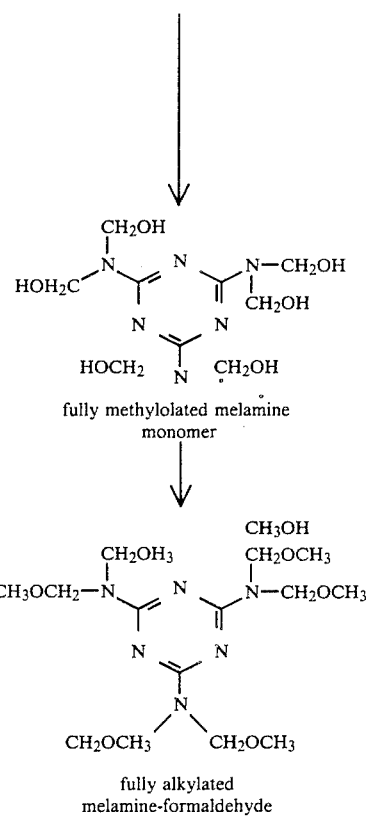

fully methylolated melamine monomer fully alkylated melamine-formaldehyde

The aforesaid condensates of melamine with formaldehyde can vary widely with respect to molecular weight, the lower molecular weight materials being monomers, dimers, and oligomers while the higher molecular weight materials are polymers of various degrees of polymerization. Monomeric melamine-formaldehyde condensates are preferred since being of lower molecular weight they exhibit less tendency toward gellation. However, one can control the polymerization of the melamine-condensate by careful control of reaction conditions and formaldehyde content. Although not preferred the polymeric materials can also be useful under appropriate conditions. In some instances it is desirable to prevent complete methylolation of all six melamine replaceable hydrogens. Thus, under these circumstances there will remain after reaction with formaldehyde a percentage of imino groups. This is referred to as the imino content.

The methylol groups formed as a result of the reaction with formaldehyde are prone to self-condense with other such groups thus in order to prevent this they are generally etherified or alkylated by reaction with an alcohol. This results in a much more stable material. The alcohol utilized for alkylation is preferably methanol. Since, as was stated previously, melamine is hexafunctional in its reaction with formaldehyde there are a total of six methylol groups or potential sites on each melamine available for alkylation, although they are not all necessarily alkylated. The degree of alkylation can vary considerably and is referred to as the methylol content. Therefore, melamine-formaldehyde condensates, monomeric as well as polymeric, can be partially alkylated or highly alkylated with a methylol content varying from as little as 0.5 percent to 16 percent. The choice of methylol content will depend upon the end use.

Benzoguanamine, also a substituted triazine, reacts with formaldehyde in a fashion similar to melamine. However, it possesses only four replaceable hydrogens and hence is tetrafunctional in its reaction with formaldehyde to form benzoguanamine-formaldehyde condensates.

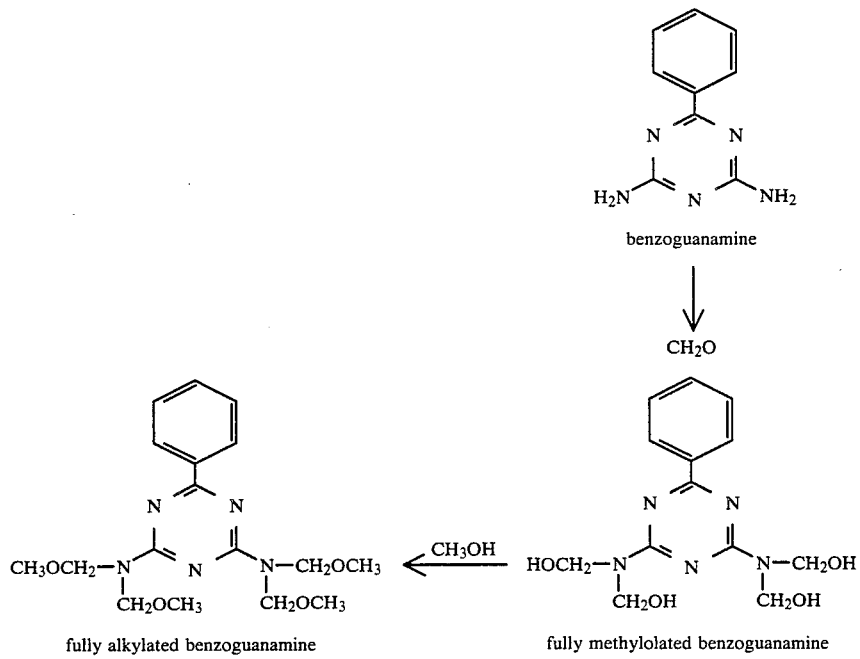

benzoguanamine → (CH₂O) → fully methylolated benzoguanamine → (CH₃OH) → fully alkylated benzoguanamine Benzoguanamine-formaldehyde condensates can also be monomeric or polymeric with varying degrees of polymerization. As monomers the condensates are available in fully alkylated form and in polymeric form the condensates are also typically fully alkylated.

Glycolurils are also very useful as condensates with formaldehyde. The following scheme is illustrative of their formation, condensation with formaldehyde and subsequent etherification to form the alkylated condensate.

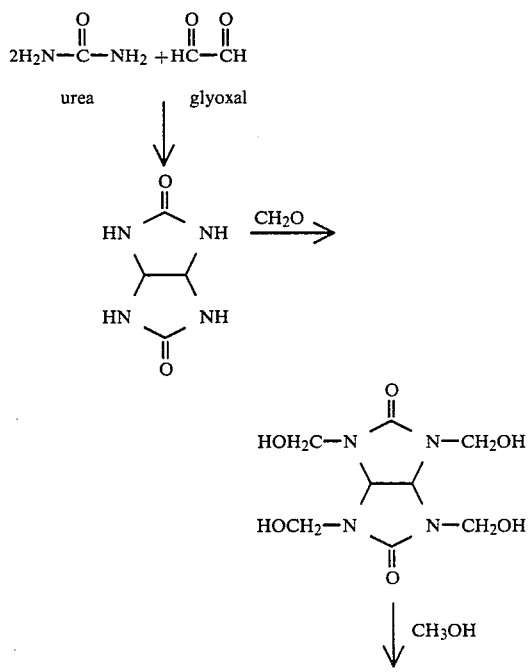

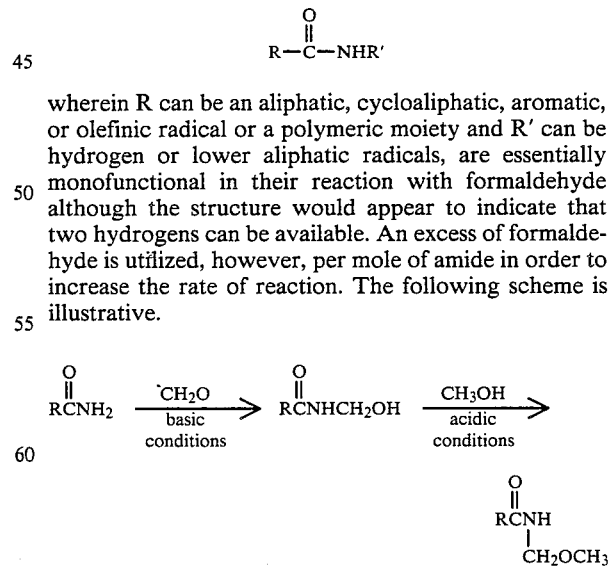

Glycoluril-formaldehyde condensates are generally monomeric and can be alkylated to any desired degree.

Amides, having the structure $$\underset{\text{O}}{\overset{\|}{R-C-NHR'}}$$

wherein R can be an aliphatic, cycloaliphatic, aromatic, or olefinic radical or a polymeric moiety and R' can be hydrogen or lower aliphatic radicals, are essentially monofunctional in their reaction with formaldehyde although the structure would appear to indicate that two hydrogens can be available. An excess of formaldehyde is utilized, however, per mole of amide in order to increase the rate of reaction. The following scheme is illustrative.

$$\underset{\text{O}}{\overset{\|}{RCNH_2}} \xrightarrow[\text{basic conditions}]{CH_2O} \underset{\text{O}}{\overset{\|}{RCNHCH_2OH}} \xrightarrow[\text{acidic conditions}]{CH_3OH}$$

$$\underset{\text{O}}{\overset{\|}{RCNH}}\\ |\\ CH_2OCH_3$$

The reaction with formaldehyde can be carried out under acidic or basic conditions, however basic conditions give a more controllable reaction product, since the competing polymerization of the methylol groups is minimized. The etherification reaction is acid catalyzed and the degree of etherification controlled by the temperature, pH and quantity of alcohol. Low temperature, low pH, and excess alcohol all favor alkylation.

As is evidenced by the structural formula set out above, amide-formaldehyde condensates can be polymeric as well as monomeric. To form a polymeric material one can, for example, react an amide such as acrylamide with formaldehyde and an alcohol to produce an N-alkoxyacrylamide which can then be copolymerized by addition polymerization of the double bonds. Alternatively, one can initially prepare an addition polymer from acrylamide and other polymerizable monomers and subsequently formylate and alkylate this polymeric material.

Urea,

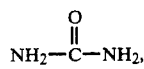

can react with formaldehyde to form either a monomethylol condensate or a dimethylol condensate. The following scheme is illustrative.

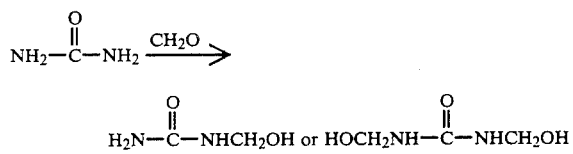

The methylolation reaction proceeds best under alkaline conditions. At acidic pH values the polymerization of the methyol ureas is much faster than the methylolation, thus polymeric condensate is formed rather than monomeric. As has been discussed above for the other types of condensates, urea-formaldehyde resins are generally unstable in the methylol form hence they too are etherified with an alcohol. Preferably butanol is utilized.

Phenol is potentially trifunctional in its reaction with formaldehyde to form phenol-formaldehyde condensates. Substituents on the phenol ring influence the rate of the methylolation reaction; in general any substituent group that increases the electron density of the ring enhances the reaction while electron withdrawing groups reduce the incidence of the reaction. Phenol-formaldehyde condensates can also be monomeric or polymeric with varying degrees of alkylation. The ratio of formaldehyde to phenol and the reaction conditions affect the relative rates of methylolation and polymerization. Generally, alkaline conditions and high formaldehyde to phenol ratio favors methylolation while a low pH and formaldehyde to phenol ratios of less than 1 favor polymerization.

The alkyl substituted piperidine-containing material of formula (I) having at least one group selected from hydroxyl, carboxyl, amido, and ureido preferably contains a hydroxyl group in the 4-position of the piperidine ring. Such suitable functional alkyl substituted piperidines, for example hydroxyl functional 2,2,6,6-tetra-alkylpiperidines, can be prepared by reaction of the 4-hydroxy-piperidine or 4-aminopiperidine with various electrophilic substrates, for example, lactones such as butyrolactone and epsilon-caprolactone, cyclic carbonates such as ethylene carbonate and propylene carbonate, epoxy materials such as ethylene oxide and propylene oxide or glycidyl ethers such as butyl glycidyl ether and allyl glycidyl ether.

For example, materials of the type represented below by formula (II) can be prepared by the reaction of a 4-hydroxy piperidine with a lactone.

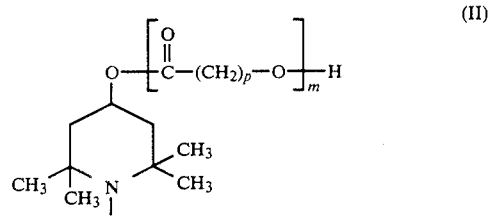

Preferably m is an integer of from 1 to 5 in order to yield high levels of hindered amine. The value of m can be determined by the mole ratio of lactone to starting alcohol; p is an integer from 2 to 5. A catalyst is usually necessary for the reaction to proceed and any of the well known catalysts such as mineral acids, organic acids, sulfonic acids, tin compounds, and titanates can be used.

Materials of the type represented by formula (III) can be prepared by reacting a 4-aminopiperidine with a lactone.

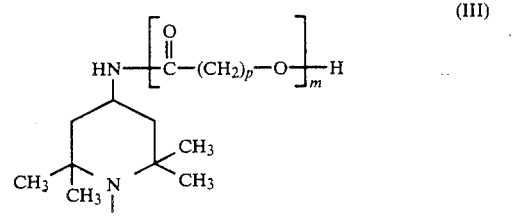

Again the value of m is preferably an integer from 1 to 5 and it can be determined by the mole ratio of lactone to starting alcohol. This type of compound can be more readily prepared without the necessity for catalyst or, if utilized, small quantities will suffice.

Materials of the type represented by formulas (IV) and (V) can be prepared by reaction of the 4-hydroxypiperidine and the 4-aminopiperidine, respectively, with carbonates.

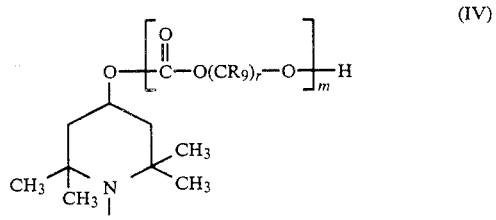

-continued

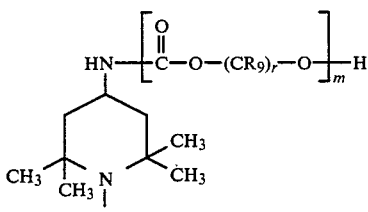
(V)

The $R_9$, m and r are as defined above, with m preferably being an integer from 1 to 5. Again, as above, the value of m can be determined from the mole ratio of reactants. A catalyst is typically utilized, for example, mineral acids, organic acids, sulfonic acids, tin compounds, and titanates.

Materials of the type represented by formulas (VI) and (VII) can be prepared by reaction of a 4-hydroxypiperidine or 4-aminopiperidine with epoxies.

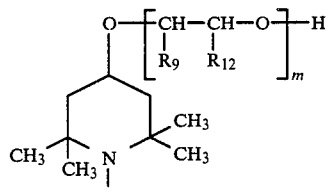
(VI)

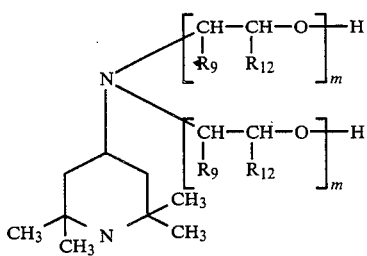
(VII)

Again, m and $R_9$ and $R_{12}$ are as defined above and the value of m can be determined from the mole ratio of reactants. A catalyst is typically utilized, for example Lewis acids or bases, e.g., benzyldimethylamine.

The ultraviolet light stabilizers of the present invention can be represented by the following structural formula:

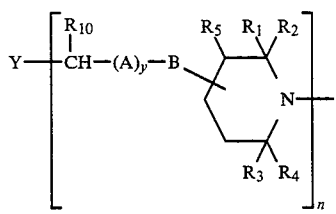
(VIII)

wherein Y, A, y, B, $R_1$, $R_2$, $R_3$, $R_4$, $R_5$, and $R_{10}$ are as defined above, and n is an integer from 1 to 6. In one embodiment the N which forms the piperidine ring can be substituted with a substituent $R_6$ which is defined as above.

The aforesaid ultraviolet stabilizers can be prepared by contacting a methylol or alkoxy alkyl-containing material such as has been described above with an alkyl substituted piperidine-containing material of formula (I) as has been set forth and described above. The above materials are contacted under conditions sufficient to transetherify and eliminate water or alcohol. In a preferred embodiment the methylol or alkoxy alkyl containing material is contacted with a hydroxyl-containing alkyl substituted piperidine of the structure:

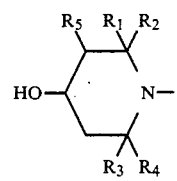
(IX)

wherein $R_1$, $R_2$, $R_3$, $R_4$ and $R_5$ are as defined above. The aforesaid hydroxyl-containing piperidine moiety is the active ultraviolet stabilizing species.

The aforesaid hydroxyl-containing alkyl substituted piperidine can be prepared from an ester having at least one group of the structure:

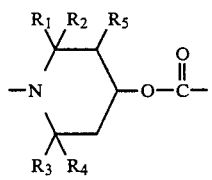
(X)

wherein $R_1$, $R_2$, $R_3$, $R_4$ and $R_5$ are as defined above.

Preferably the aforesaid ester is a diester of the formula

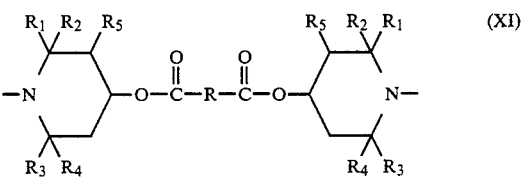
(XI)

wherein $R_1$ through $R_5$ are as defined above and R is alkylene, alkenylene, alkynylene, arylene, or phenylene, preferably $C_1$ to $C_{12}$ alkylene. The TINUVIN series of materials which are commercially available from Ciba-Geigy Corp. including TINUVIN 292, TINUVIN 770, and those esters described in U.S. Pat. No. 3,640,928 to Muryama et al. are quite useful as the diester.

Preferably the aforesaid diester is contacted with a polyol or an amine, including amino alcohols, under conditions sufficient for alcoholysis or aminolysis of the ester to form a reaction mixture having as a component a hydroxyl-containing alkyl substituted piperidine material of the formula (IX) and an amide diol or ester diol. An amount of amine, alcohol, or amino alcohol is utilized which is sufficient to alcoholyze or aminolyze all of the ester groups of the piperidine diester. Generally one equivalent of the amine or alcohol is utilized for each ester group present. It is preferred that excess amine not be present as this requires subsequent neutralization. The amine can be a primary or secondary mono-, di, or triamine or amino alcohol. The polyol is preferably a diol. Suitable diols include $C_2$ to $C_{10}$ diols such as ethylene glycol, propylene glycol, butylene glycol, neopentyl glycol, hexanediol, diethylene glycol, 1,5-pentanediol, and 1,4-cyclohexane dimethanol. Suitable amines include monoethanolamine, propanolamine, and primary and secondary alkyl substituted monoamines, diamines, and triamines. Either material is heated with the diester to a temperature of from about 100° C. to about 200° C. to reflux and the progress of the reaction is monitored by a variety of art-recognized methods. For example, the aminolysis reaction can be monitored by repeated amine equivalent weight determinations at selected intervals. It is this reaction mixture which is reacted with a methylol or alkoxy alkyl, preferably alkoxy methyl, containing material, as described above, to form a second reaction mixture containing as a component the alkyl substituted piperidine ultraviolet light stabilizer of formula (VIII).

For example, in one preferred embodiment, a methylated melamine-formaldehyde condensate is transetherified with 1,2,2,6,6-pentamethyl-4-hydroxypiperidine through the active hydrogen of the 4-hydroxypiperidine to form an ultraviolet light stabilizer of the following structural formula:

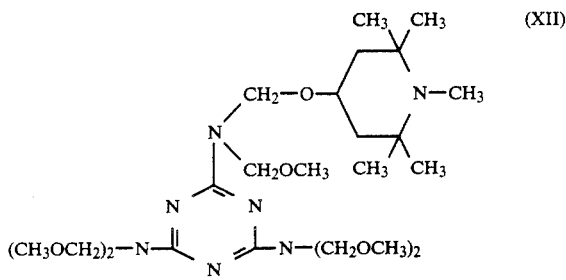

(XII)

The reaction is carried out by heating to a temperature of from about 75° C. to about 150° C. thus removing the distillation alcohol when a fully alkylated methylol containing material is utilized and any water which might be liberated from non-alkylated portions of a partially alkylated material. In this regard it is noteworthy that the alkylated methylol-containing material should be chosen such that the alkylating alcohol that was employed in its preparation has up to six carbons. Higher molecular weight alcohols require more heat to remove them in the aforesaid process hence promoting the risk of gellation.

The etherification reaction to form the reaction mixture containing as a component the stabilizer of formula (VII) is generally acid catalyzed. The type and identity of the acid catalyst is not critical and any of the acid catalysts conventionally utilized in the coatings art may be employed herein. Some examples of suitable catalysts include methanesulfonic acid, paratoluenesulfonic acid, formic acid, naphthalene sulfonic acid, phosphoric acid, hydrochloric acid, oxalic acid, and butyl hydrogen phosphate.

Sufficient acid catalyst is used to neutralize the piperidinyl nitrogen when it is substituted with hydrogen, alkyl, or aryl. When the nitrogen is substituted with, for example, acyl or carbamoyl groups, the nitrogen does not exhibit basicity hence neutralization by additional acid catalyst is not necessary.

The reaction is typically carried out in the absence of solvent; however one can be utilized. Useful solvents are those which are inert to the reactants and which are relatively high boiling. Suitable materials include toluene, xylene, methyl isobutyl ketone, diisoamyl ketone and cyclohexanone.

The ratio of piperidinol to formaldehyde condensate is preferably such that an excess of formaldehyde condensate is present. This is preferred in order that some methylol or alkoxy alkyl groups will remain to be available for crosslinking during film-formation.

The equivalent weight of the formaldehyde condensate can be determined by an NMR technique. The principal involved in determining the equivalent weight of the formaldehyde condensate by NMR involves measuring the area under the NMR signal due to the hydrogen in the aldehyde portion of the condensate. For example when the formaldehyde condensate is formed from an amide or amine, e.g., melamine, and formaldehyde, the methylene groups derived from the formaldehyde in the melamine resin would include —CH$_2$OH; —CH$_2$OR; —OCH$_2$N— and —NCH$_2$N—. These methylene groups give proton NMR signals in the region around 4.5 to about 5.5 ppm down field from TMS (tetramethylsilane used as reference for chemical shift). The area of the CH$_2$ signals is directly proportional to the quantity of CH$_2$ groups present in the resin.

To avoid interference from NMR signals of solvents present in the formaldehyde condensate, toluene is used as an external reference material. Both the toluene and formaldehyde condensated NMR spectra are recorded under identical experimental conditions. The integrated area of the CH$_2$ groups of the melamine resin, for example, is compared directly to the area of the methyl groups of toluene. The equivalent weight of the resin per mole of CH$_2$ is calculated directly from the ratio of the area in a known concentration of toluene.

The alkyl substituted piperidine ultraviolet light stabilizers detailed above and prepared in accordance with the process described above are useful as additives in resinous compositions comprising an active hydrogen-containing material and a curing agent reactive with the active hydrogens to form a cured product. A fundamental aspect of the present invention is that the aforesaid ultraviolet light stabilizers react with the active hydrogen-containing resinous component and curing agent to become chemically incorporated into the cured material. In this manner the ultraviolet light stabilizer is prevented from release by volatilization and the cured material has optimum ultraviolet light stabilization. This is particularly evidenced by the excellent gloss retention exhibited by coating compositions containing the claimed ultraviolet light stabilizers which have been exposed to accelerated weathering. This is quite different from conventional ultraviolet light stabilizing additives which are merely added to resinous compositions but are not chemically incorporated in them. These conventional stabilizers readily volatilize and escape from the cured material.

Suitable active hydrogen containing materials are all of these conventionally known and utilized in the art of preparing resinous compositions. For example polyester polyols and acrylic polyols are excellent for use herein. These polyols are described in detail in column 3, lines 64 to 68, column 4, lines 1 to 68, and column 5, lines 1 to 19 of U.S. Pat. No. 4,154,891 the disclosure being incorporated by reference herein.

The curing agent is one capable of reacting with the active hydrogens, such as aminoplast, phenoplast, and blocked isocyanate curing agents which are well known and conventionally utilized. The aforesaid aminoplast, phenoplast, and blocked isocyanate curing agents are described in detail in column 5, lines 34 to 68, and column 6, lines 1 to 32 of U.S. Pat. No. 3,919,351 and disclosure being incorporated by reference herein.

It should be understood that the curing agent which is utilized to react with the active hydrogen containing material has no piperidine moieties associated with it.

The resinous compositions of the present invention ordinarily contain other optional ingredients such as pigments, fillers, plasticizers, flow control agents and other formulating additives.

It should be noted that if desired the ultraviolet light stabilizers of the present invention can also be utilized in thermoplastic resinous compositions.

The ultraviolet stabilizers can be used not only in resinous compositions which are coating compositions but also other resinous compositions such as molding and laminating compositions. Typically, the ultraviolet light stabilizers are utilized in all types of melamine curable coating compositions with high requirements for durability, e.g., coil coatings, automotive coatings, and aluminum extrusion coatings. Usually the hindered amine ultraviolet light stabilizers are present in an amount ranging from 0.1 to 5 percent by weight based on the resinous components of the compositions.

The following examples are submitted for the purpose of further illustrating the nature of the present invention and should not be construed as a limitation on the scope thereof. All parts and percentages in the Examples and throughout the specification are by weight unless otherwise indicated.

EXAMPLE I

Preparation of 1,2,2,6,6-Pentamethyl-4-Hydroxy Piperidine

Into a reactor vessel equipped with a stirrer, reflux condenser and nitrgoen blanket were charged 2224 parts of TINUVIN 292 having the following structure

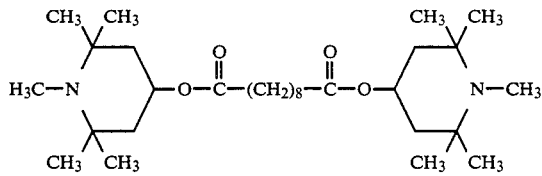

(commercially available from Ciba-Geigy Corp.) and 534 parts of monoethanolamine. The mixture was heated to a temperature of 155° C. to reflux, maintained at reflux for a period of 12 hours and then cooled. The progress of the reaction was monitored by amine equivalent determinations at selected intervals. (The determinations were performed by titrating a sample of the reaction mixture with 0.3N HCl in ethylene glycol monoethyl ether.) The resultant reaction product was a mixture of 54 percent by weight 1,2,2,6,6-pentamethyl-4-hydroxy piperidine, having the following structure

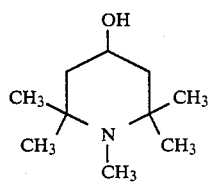

and 46 percent by weight of an amide diol.

EXAMPLE II

Preparation of a melamine-formaldehyde/1,2,2,6,6-pentamethyl-4-hydroxy piperidine ultraviolet light stabilizer Into a reactor vessel equipped with a stirred, reflux condenser, and addition funnel were charged 115.3 parts of the hydroxy piperidine reaction mixture of Example I, above, and 285.5 parts of an essentially monomeric melamine-formaldehyde resin (commercially available from American Cyanamid Company as CYMEL 303). These ingredients were mixed together following the addition of 0.4 parts of triphenylphosphate and 16.8 parts of formic acid. The entire mixture was heated to 150° C. for about 30 minutes with the evolution of 23 milliliters of methanol. The resultant melamine-formaldehyde/hydroxy piperidine condensate was cooled and thinned to a solids content of 75 percent by the addition of 133 parts of methyl isobutyl ketone.

EXAMPLE III

Preparation of a urea-formaldehyde/1,2,2,6,-pentamethyl-4-hydroxy piperidine ultraviolet light stabilizer Into a reactor vessel equipped with a stirrer, reflux condenser, and addition funnel were charged 416.5 parts of the hydroxy piperidine reaction mixture of Example I above, and 528.9 parts of an essentially monomeric urea-formaldehyde resin (commercially available from American Cyanamid Company as BEETLE 65). The aforesaid ingredients were heated to 125° C. to form a homogeneous mixture followed by the addition of 60.6 parts of formic acid. Heating was continued for about 90 minutes with the evolution of 90 milliliters of methanol. The resultant urea formaldehyde/hydroxy piperidine condensate was cooled and thinned to a solids content of 80 percent by the addition of 235 parts of ethanol.

EXAMPLE IV

Preparation of a benzoguanamine/1,2,2,6,6-pentamethyl-4-hydroxy piperidine ultraviolet light stabilizer Into a reactor vessel equipped with a stirrer, reflux condenser, and addition funnel were charged 255.1 parts of the hydroxy piperidine reaction mixture of Example I, above, and 744.9 parts of an essentially monomeric benzoguanamine resin (commercially available from American Cyanamide Company as CYMEL 1123). The aforesaid ingredients were heated to 130° C. to form a homogeneous mixture followed by the addition of 87.1 parts of formic acid. Heating was continued for a period of 12 hours with the evolution of 47 milliliters of methanol. The resultant benzguanamine/hydroxy piperidine condensate was cooled and thinned to a solids content of 80 percent by the addition of 254 parts of ethanol.

EXAMPLE V

Preparation of a glycoluril/1,2,2,6,6-pentamethyl-4-hydroxy piperidine ultraviolet light stabilizer Into a reactor vessel equipped with a stirrer, reflux condenser, and addition funnel where charged 328.5 l parts of the hydroxy piperidine reaction mixture of Example I, above, and 671.5 parts of an essentially monomeric glycoluril resin (commercially available from American Cyanamide Company as CYMEL 1171). The aforesaid ingredients were heated to 140° C. to form a homogeneous mixture followed by the addition of 47.8 parts of formic acid. Heating was continued for a period of 12 hours with the evolution of 59 milliliters of methanol. The resultant glycoluril/hydroxy piperidine reaction mixture was cooled and thinned to 80 percent solids by the addition of 251 parts of ethanol. This was further thinned to 50 percent solids by the addition of N-methylpyrollidinone.

EXAMPLE VI

In this example the ultraviolet light stabilizers prepared in EXAMPLES II to V, above, were incorporated into both an acrylic and polyester resin based coating composition. The coating compositions were spray applied to primed metal panels, cured by baking at 250° F. (121° C.) for 30 minutes and evaluated for initial gloss. Gloss was measured with a GARDNER GLOSSMETER at 20°. The cured panels were then subjected to exposure in a QUV Accelerated Weathering Tester (supplied by Q-Panel Company in Cleveland, Ohio). The exposure consisted of alternating cycles of humidity (4 hours at 50° C.) and light (8 hours at 70° C.). The panels were periodically evaluated for gloss (retained gloss) in the manner described above. Percent Gloss Retention was calculated from the following formula:

(Retained Gloss/Initial Gloss) × 100%

The results are set out in Table I.

(a) The acrylic resin based coating composition for each example had a total solids content of 60 percent and was formulated in the following fashion. The coating composition was reduced to spray viscosity of 22 seconds (#4 Ford Cup) with methyl amyl ketone.

| Ingredients | Parts by Weight (grams) |
| --- | --- |
| Acrylic Resin[1] | 100.0 |
| Pigment Paste[2] | 100.0 |
| CYMEL 303 crosslinking agent[3] | 30 |
| Microgel flow control agent | 11.4 |

| Ingredients | Parts by Weight (grams) |
| --- | --- |
| Acid catalyst[4] | 1.75 |
| Cellulose acetate butyrate | 4 |
| Methyl amyl ketone | 28.35 |

(b) The polyester resin based coating composition composition for each example had a total solids content of 59 percent, and was formulated in the following fashion. The coating composition was reduced to spray viscosity of 17 seconds (#4 Ford Cup) with a mixture of 80 parts by volume, of 2-ethoxyethanol acetate and 20 parts by volume of isobutyl acetate.

| Ingredients | Parts by Weight (grams) |
| --- | --- |
| Polyester Resin[5] | 76.9 |
| Pigment Paste[6] | 105.0 |
| CYMEL 303 crosslinking agent | 30 |
| Microgel flow control agent | 11.4 |
| Acid catalyst[7] | 1.75 |
| Cellulose acetate butyrate[8] | 4 |
| 2-butoxyethanol acetate | 10 |
| 2-ethoxyethanol acetate | 14.45 |
| AROMATIC 100[9] | 8 |
| n-propanol | 11 |

(c) These ultraviolet light stabilizer-containing coating compositions were prepared by adding 3 parts by weight (containing 0.5 percent TINUVIN 292) of the condensate to each of the base coating compositions, (a) and (b).

(d) These ultraviolet light stabilizer-containing coat-

TABLE I

| Ultraviolet Light Stabilizer | Base Coating Composition | Initial Gloss | Retained Gloss 144 Hours | Percent Gloss Retention | Retained Gloss 490 Hours | Percent Gloss Retention | Retained Gloss 748 Hours | Percent Gloss Retention |
| --- | --- | --- | --- | --- | --- | --- | --- | --- |
| Melamine-formaldehyde type:[c] CYMEL 303/1,2,2,6,6-pentamethyl-4-hydroxy piperidine condensate | Acrylic[a] Polyester[b] | 81 74 | 60 27 | 74 36 | 62 | 76 | 26 | 32 |
| Urea-formaldehyde type:[d] BEETLE 65/1,2,2,6,6-pentamethyl-4-hydroxy piperidine condensate | Acrylic Polyester | 86 70 | 67 18 | 78 26 | 61 | 71 | 24 | 28 |
| Benzoguanamine type:[e] CYMEL 1123/1,2,2,6,6-pentamethyl-4-hydroxy piperidine condensate | Acrylic Polyester | 85 81 | 77 36 | 91 44 | 67 | 79 | 30 | 35 |
| Glycoluril type:[f] CYMEL 1171/1,2,2,6,6-pentamethyl-4-hydroxy piperidine condensate | Acrylic Polyester | 83 81 | 81 46 | 97 57 | 76 | 92 | 66 | 80 |
| TINUVIN 292[g] | Acrylic Polyester | 80 60 | 73 20 | 91 33 | 47 | 59 | 14 | 18 |
| None (control)[h] | Acrylic Polyester | 75 58 | 70 8 | 93 14 | 52 | 74 | 18 | 24 | ing compositions were prepared by adding 3 parts by weight (containing 0.5 percent TINUVIN 292) of the condensate to each of the base coating compositions (a) and (b).

(e) These ultraviolet light stabilizer-containing coating compositions were prepared by adding 3.15 parts by weight (containing 0.5 percent TINUVIN 292) of the condensate to each of the base coating compositions (a) and (b).

(f) These ultraviolet light stabilizer-containing coating compositions were prepared by adding 3.96 parts by weight (containing 0.5 percent TINUVIN 292) of the condensate to each of the base coating compositions (a) and (b).

(g) These coating compositions each contained 1 part by weight (1.0 percent) of TINUVIN 292) physically admixed therein.

(h) These control coating compositions contained no ultraviolet light stabilizer.

Although the invention has been described with specific references and specific details of embodiments thereof, it is to be understood that it is not intended to be so limited since changes and alterations therein may be made by those skilled in the art which are within the full intended scope of this invention as defined by the appended claims.

We claim:

1. A reaction product which comprises a material formed from the reaction of
   (a) a methylol or alkoxy alkyl-containing material which is represented by the following structural formula:

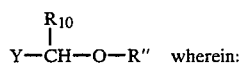
   wherein:

R″ is hydrogen or $C_1$ to $C_6$ alkyl,
   $R_{10}$ is hydrogen or methyl
   Y is a radical derived from a material selected from the group consisting of amino substituted triazines, ureas, glycolurils, phenols, and amides of the formula:

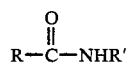

wherein:
   R′ is hydrogen or $C_1$ to $C_{12}$ alkyl and R is an aliphatic, cycloaliphatic, or olefinic radical, or an acrylic polymer moiety; and
   (b) an alkyl substituted piperidine-containing material having at least one group selected from hydroxyl, carboxyl, amido, and ureido, said reaction proceeding between a methylol or alkoxy alkyl group of (a) and the group selected from hydroxyl, carboxyl, amido and ureido of (b).

2. The reaction product of claim 1 wherein Y is derived from melamine or benzoguanamine.

3. The reaction product of claim 1 wherein Y is derived from urea.

4. The reaction product of claim 1 wherein the alkyl substituted piperidine-containing material having at least one group selected from hydroxyl, carboxyl, amido, and ureido is represented by the following structural formula:

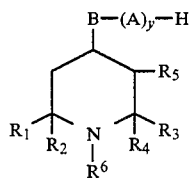

wherein B is oxygen or

wherein $R_{11}$ is hydrogen, $C_1$ to $C_4$ alkyl, $-(A)_y-H$ or

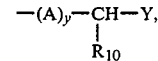

wherein $R_{10}$ is hydrogen or methyl and and Y is a radical derived from a material selcted from the group consisting of amino substituted triazines, ureas, glycolurils, phenols, and amides of the formula

 wherein

R′ is hydrogen or $C_1$ or $C_{12}$ alkyl and R is an aliphatic, cycloaliphatic, or olefinic radical, or an acrylic polymer moiety; $R_1$, $R_2$, $R_3$, $R_4$ are the same or different $C_1$ to $C_6$ alkyl, and $R_1$ and $R_2$ when joined together form a $C_3$ to $C_{12}$ cycloaliphatic ring; $R_5$ is hydrogen or methyl; $R_6$ is hydrogen, O, $C_1$ to $C_{12}$ alkyl, hydroxyl, $C_2$ to $C_{18}$ alkenyl or alkynyl, $C_7$ to $C_{18}$ aralkyl, acyl, carbamyl, benzyl, or a group $$\left[-(CH_2)_qHC-O-\atop R_7\right]_w-H$$

wherein $R_7$ is hydrogen, methyl, ethyl, phenyl, or $CH_2OR_8$, q is an integer from 1 to 3 and w is an integer from 1 to 10 and $R_8$ is $C_1$ to $C_6$ alkyl or phenyl;
   A is

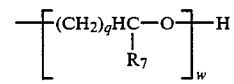;

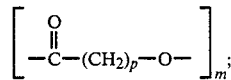;

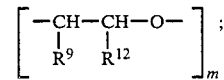 ; or

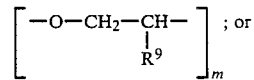

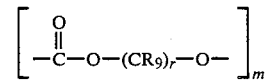

wherein $R_9$ and $R_{12}$ are independently hydrogen or $C_1$ to $C_{10}$ alkyl; m is an integer from 1 to 10; p is an integer from 1 to 5; r is an integer from 2 to 3; and y is 0 or 1 with the proviso that when B is $R_{11}N-$, y is 1.

5. A reaction product which comprises a material formed from the reaction of:
   (a) a methylol or alkoxy alkyl containing material which is represented by the following formula:

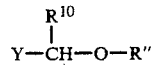

wherein R'' is hydrogen or $C_1$ to $C_6$ alkyl;

(b) an alkyl substituted piperidine-containing material having at least one group selected from hydroxyl, carboxyl, amido, and ureido, said reaction proceeding between a methylol or alkoxy alkyl group of (a) and the group selected from hydroxyl, carboxyl, amido or ureido of (b), said material formed from the reaction of (a) and (b) having the following structural formula:

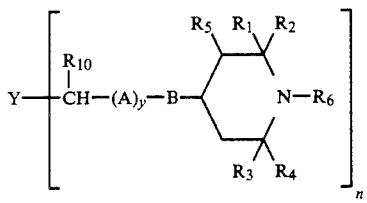

wherein; Y is a radical derived from a material selected from the group consisting of amino substituted triazines, ureas, glycolurils, phenols, and amides of the formula

 wherein

R' is hydrogen or $C_1$ to $C_{12}$ alkyl and R is an aliphatic, cycloaliphatic, or olefinic radical, or an acrylic polymer moiety; $R_1$, $R_2$, $R_3$, $R_4$ are the same or different $C_1$ to $C_6$ alkyl; and $R_1$ and $R_2$ when joined together to form a $C_3$ to $C_{12}$ cycloaliphatic ring; $R_5$ is hydrogen or methyl; $R_6$ is hydrogen, O; $C_1$ to $C_{12}$ alkyl, hydroxyl, $C_2$ to $C_{18}$ alkenyl or alkynyl, $C_7$ to $C_{18}$ aralkyl, acyl, carbamyl, benzyl, or a group

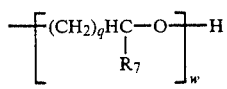

$R_7$ is hydrogen, methyl, ethyl, phenyl, or $CH_2OR_8$, q is an integer from 1 to 3 and w is an integer from 1 to 10 and $R_8$ is $C_1$ to $C_6$ alkyl or phenyl;
$R_{10}$ is hydrogen or methyl;
B is oxygen or

wherein $R_{11}$ is hydrogen, $C_1$ to $C_4$ alkyl, $-(A)_yH$, or

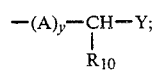

A is

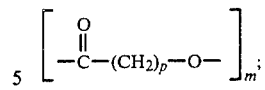

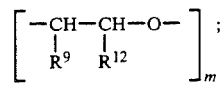

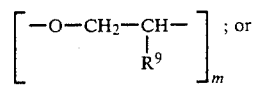

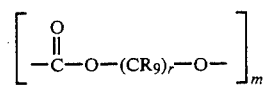

wherein $R_9$ and $R_{12}$ are independently hydrogen or $C_1$ to $C_{10}$ alkyl; m is an integer from 1 to 10; p is an integer from 1 to 5; r is an integer from 2 to 3; n is an integer from 1 to 6; and y is 0 or 1, with the proviso that when B is

y is 1.

6. The reaction product of claim 5 wherein $R_1$, $R_2$, $R_3$ $R_4$ are each methyl, $R_5$ is hydrogen, $R_6$ is methyl and B is oxygen.

7. The reaction product of claim 5 wherein $R_1$, $R_2$, $R_3$, $R_4$ are each methyl, $R_5$ is hydrogen, $R_6$ is hydrogen, and B is oxygen.

8. The reaction product of claim 5 wherein Y is a radical derived from melamine or benzoquanamine.

9. The reaction product of claim 5 wherein Y is derived from urea.

10. A reaction product which comprises a material formed from the reaction of (a) a methylol or alkoxy alkyl containing material which is represented by the following formula:

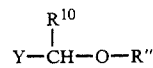

wherein R'' is hydrogen or $C_1$ to $C_6$ alkyl;

(b) an alkyl substituted piperidine-containing material having at least one group selected from hydroxyl, carboxyl, amido, and ureido, said reaction proceeding between a methylol or alkoxy alkyl group of (a) and the group selected from hydroxyl, carboxyl, amido or ureido of (b), said material formed from the reaction product of (a) and (b) having the following structural formula:

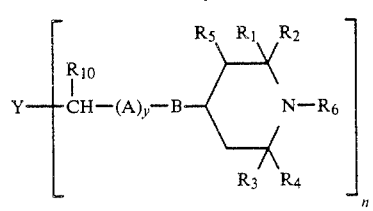

wherein
Y is a radical derived from glycoluril;
$R_1$, $R_2$, $R_3$, $R_4$ are the same or different $C_1$ to $C_6$ alkyl; and $R_1$ and $R_2$ when joined together form a $C_3$ to $C_{12}$ cycloaliphatic ring;
$R_5$ is hydrogen or methyl
$R_6$ is hydrogen, O, $C_1$ to $C_{12}$ alkyl, hydroxyl, $C_2$ to $C_{18}$ alkenyl or alkynyl, $C_7$ to $C_{18}$ aralkyl, acyl, carbamyl, benzyl, or a group

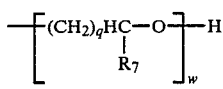

$R_7$ is hydrogen, methyl, ethyl, phenyl, or $CH_2OR_8$, q is an integer from 1 to 3 and w is an integer from 1 to 10 and
$R_8$ is $C_1$ to $C_6$ alkyl or phenyl;
$R_{10}$ is hydrogen or methyl;
B is oxygen or

wherein $R_{11}$ is hydrogen, $C_1$ to $C_4$ alkyl, $-(A-)_y-H$, or

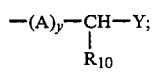

A is

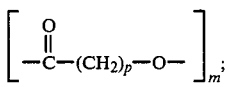

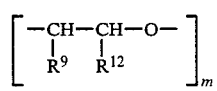

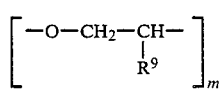

wherein $R_9$ and $R_{12}$ are independently hydrogen or $C_1$ to $C_{10}$ alkyl; m is an integer from 1 to 10; p is an integer from 1 to 5; r is an integer from 2 to 3; n is an integer from 1 to 6; and y is 0 or 1, with the proviso that when B is

y is 1.

11. A process for the preparation of a hindered amine stabilizer, comprising contacting a methylol or alkoxy alkyl containing material with an alkyl substituted piperidine containing material of the structure:

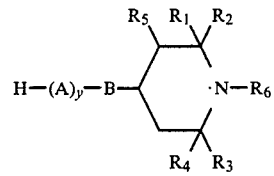

under conditions sufficient to transetherify and eliminate water or alcohol, thereby forming a hindered amine stabilizer having the following structural formula:

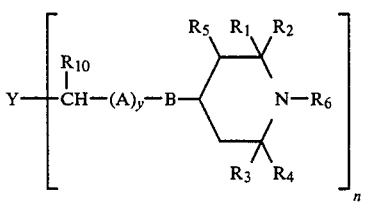

wherein: Y is a radical derived from a material selected from the group consisting of amino substituted triazines, ureas, glycolurils, phenols, and amides of the formula

 wherein wherein R' is hydrogen or $C_1$ to $C_{12}$ alkyl and R is an aliphatic, cycloaliphatic, or olefinic radical, or an acrylic polymer moiety; $R_1$, $R_2$, $R_3$, $R_4$ are the same or different $C_1$ to $C_6$ alkyl; and $R_1$ and $R_2$ when joined together to form a $C_3$ to $C_{12}$ cycloaliphatic ring; $R_5$ is hydrogen or methyl; $R_6$ is hydrogen, O; $C_1$ to $C_{12}$ alkyl, hydroxyl, $C_2$ to $C_{18}$ alkenyl or alkynyl, $C_7$ to $C_{18}$ aralkyl, acyl, carbamoyl, benzyl, or a group

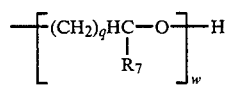

$R_7$ is hydrogen, methyl, ethyl, phenyl, or $CH_2OR_8$, q is an integer from 1 to 3 and w is an integer from 1 to 10 and
$R_8$ is $C_1$ to $C_6$ alkyl or phenyl;
$R_{10}$ is hydrogen or methyl;
B is oxygen or

wherein $R_{11}$ is hydrogen, $C_1$ to $C_4$ alkyl, $-(A-)_y-H$, or

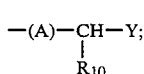

A is

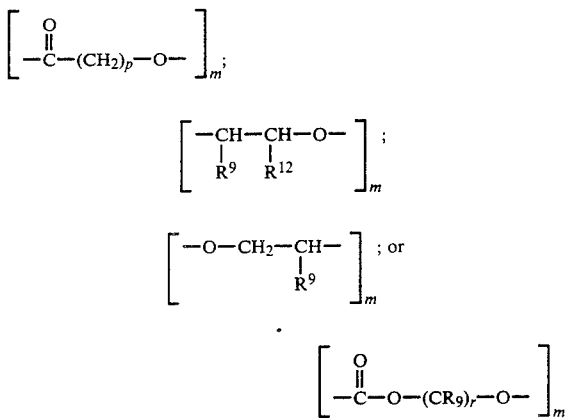

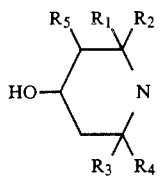

wherein $R_9$ and $R_{12}$ are independently hydrogen or $C_1$ to $C_{10}$ alkyl; m is an integer from 1 to 10; p is an integer from 1 to 5; r is an integer from 2 to 3; n is an integer from 1 to 6; and y is 0 or 1, with the proviso that when B is

y is 1.

12. The process of claim 11 wherein the alkyl substituted piperidine-containing material has the following structure:

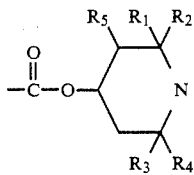

and is a component of a reaction mixture prepared by a method which comprises contacting an ester having at least one group of the structure:

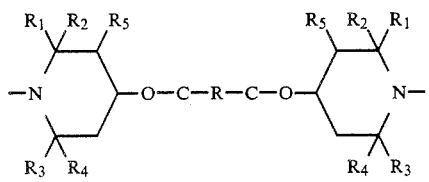

with a polyol or amino alcohol under conditions sufficient to alcoholyze or aminolyze the ester and form the reaction mixture; wherein $R_1$, $R_2$, $R_3$, $R_4$ are the same or different $C_1$ to $C_6$ alkyl; and $R_5$ is hydrogen or methyl.

13. The process of claim 12 wherein the ester is represented in the following structural formula:

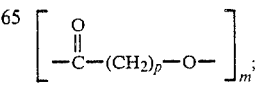

wherein R is alkylene, alkenylene, alkynlene, arylene, or phenylene.

14. In a thermosetting resinous composition comprising an active hydrogen-containing material and a curing agent reactive with the active hydrogens to form a cured product, the improvement comprising including in the composition a hindered amine of the structure:

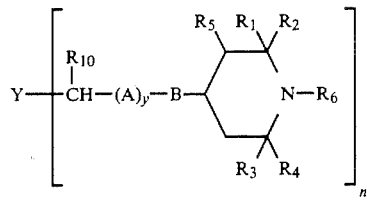

wherein:

Y is a radical derived from a material selected from the group consisting of amino substituted triazines, ureas, glycolurils, phenols, and amides of the formula

wherein

R' is hydrogen or $C_1$ to $C_{12}$ alkyl and R is an aliphatic, cycloaliphatic, or olefinic radical, or an acrylic polymer moiety;

$R_1$, $R_2$, $R_3$, $R_4$ are the same or different $C_1$ to $C_6$ alkyl; and $R_1$ and $R_2$ when joined together form a $C_3$ to $C_{12}$ cycloaliphatic ring;

$R_5$ is hydrogen or methyl;

$R_6$ is hydrogen, O, $C_1$ to $C_{12}$ alkyl, hydroxyl, $C_2$ to $C_{18}$ alkenyl or alkynyl, $C_7$ to $C_{18}$ aralkyl, acyl, carbamyl, benzyl, or a group

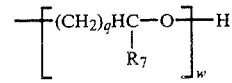

wherein $R_7$ is hydrogen, methyl, ethyl, phenyl, or $CH_2OR_3$, q is an integer from 1 to 3 and w is an integer from 1 to 10 and $R_8$ is $C_1$ to $C_6$ alkyl or phenyl;

$R_{10}$ is hydrogen or methyl;

B is oxygen or

wherein $R_{11}$ is hydrogen, $C_1$ to $C_4$ alkyl,

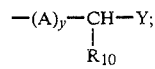

A is

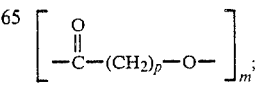

-continued

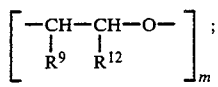

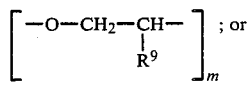

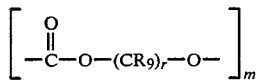

wherein $R_9$ and $R_{12}$ are independently hydrogen or $C_1$ to $C_{10}$ alkyl; m is an integer from 1 to 10; p is an integer from 1 to 5; r is an integer from 2 to 3; n is an integer from 1 to 6; and y is 0 or 1, with the proviso that when B is

y is 1.

15. The composition of claim 14 wherein the hindered amine is present in an amount ranging from 0.1 to 5 percent by weight based on the resinous components of the composition.

16. A reaction product which comprises a material formed from the reaction of:
(a) a methylol or alkoxy alkyl-containing material of the following structural formula:

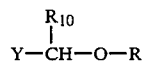

wherein Y is a radical derived from glycoluril; R is hydrogen, $C_1$ to $C_6$ alkyl, and $R_{10}$ is hydrogen or methyl;
(b) an alkyl substituted piperidine-containing material having at least one group selected from hydroxyl, carboxyl, amido, and ureido, said reaction proceeding between a methylol or alkoxy alkyl group of (a) and the group selected from hydroxyl, carboxyl, amido and ureido of (b).

* * * * *

UNITED STATES PATENT AND TRADEMARK OFFICE
CERTIFICATE OF CORRECTION

PATENT NO. : 4,696,959

DATED : September 29, 1987

INVENTOR(S) : Wen-Hsuan Chang, et al

It is certified that error appears in the above-identified patent and that said Letters Patent is hereby corrected as shown below:

Column 22, line 13, claim 4; after "methyl", delete one occurrence of "and".

Column 22, line 22, claim 4; "$C_1$ or $C_{12}$" should read --$C_1$ to $C_{12}$--.

Column 24, line 32, claim 6; after "$R_3$", insert --,--.

Column 26, line 34, claim 11; delete "wherein".

Column 26, line 42, claim 11; "carbamoyl" should read --carbamyl--.

Signed and Sealed this

Twenty-third Day of August, 1988

*Attest:*

*Attesting Officer*

DONALD J. QUIGG

*Commissioner of Patents and Trademarks*